United States Patent [19]

DeLuca et al.

[11] 4,448,721

[45] May 15, 1984

[54] HYDROXYVITAMIN $D_2$ COMPOUNDS AND PROCESS FOR PREPARING SAME

[75] Inventors: Hector F. DeLuca; Heinrich K. Schnoes; Jacek W. Morzycki, all of Madison, Wis.

[73] Assignee: Wisconsin Alumni Research Foundation, Madison, Wis.

[21] Appl. No.: 420,191

[22] Filed: Sep. 20, 1982

[51] Int. Cl.[3] .......................... C07J 43/00; C07J 9/00
[52] U.S. Cl. ........................ 260/239.5; 260/239.55 C; 260/397.2
[58] Field of Search .................... 260/397.2, 239.55 C, 260/239.5

[56] References Cited

U.S. PATENT DOCUMENTS 4,229,358  10/1980  De Luca et al. ................ 260/397.2

Primary Examiner—Elbert L. Roberts
Attorney, Agent, or Firm—Howard W. Bremer

[57] ABSTRACT

This invention relates to hydroxylated derivatives of vitamin $D_2$, to processes for preparing such compounds, to intermediates utilized in such processes and to certain isotopically labelled vitamin $D_2$ compounds.

The vitamin $D_2$ derivatives would find application in the treatment of or prophylaxsis for various disease states characterized by calcium and phosphorous imbalances and as a substitute for vitamin $D_3$ and its metabolites in their various applications.

35 Claims, No Drawings

HYDROXYVITAMIN $D_2$ COMPOUNDS AND PROCESS FOR PREPARING SAME

TECHNICAL FIELD

This invention relates to biologically active vitamin D compounds.

More specifically, this invention relates to a process for the preparation of hydroxylated derivatives of vitamin $D_2$, and to novel intermediates used in this process.

Still more specifically, this invention relates to the synthesis of 25-hydroxyvitamin $D_2$ and the 24-epimer thereof, to certain alkyl and aryl-analogs and to 5,6-trans-, and the acyl derivatives of these compounds.

BACKGROUND

The D vitamins are very important agents for the control of calcium and phosphate metabolism in animals and humans, and have long been used as dietary supplements and in clinical practice to assure proper bone growth and development. It is now known that the in vivo activity of these vitamins, specifically of vitamin $D_2$ and $D_3$, is dependent on metabolism to hydroxylated forms. Thus, vitamin $D_3$ undergoes two successive hydroxylation reactions in vivo, leading first to 25-hydroxyvitamin $D_3$ and then to 1,25-dihydroxyvitamin $D_3$ and the latter is indeed thought to be the compound responsible for the well-known beneficial effects of vitamin $D_3$. Likewise, vitamin $D_2$, which is commonly used as a dietary supplement, undergoes an analogous hydroxylation sequence to its active forms, being first converted to 25-hydroxyvitamin $D_2$ (25—OH—$D_2$) and then to 1,25-dihydroxyvitamin $D_2$ (1,25—(OH)$_2D_3$). These facts are well established and well known in the art [see, for example, Suda et al. Biochemistry 8, 3515 (1969) and Jones et al. Biochemistry 14, 1250 (1975)].

Like the metabolites of the vitamin $D_3$ series, the hydroxylated forms of vitamin $D_2$ named above are, because of their potency and other beneficial properties, highly desirable dietary supplements, or pharmaceutical agents, for the cure or prevention of bone or related diseases, and their value and possible use is recognized in patents relating to these compounds [U.S. Letters Pat. Nos. 3,585,221 and 3,880,894].

Whereas all metabolites of vitamin $D_3$ have been prepared by chemical synthesis, there has been but little work on the preparation of vitamin $D_2$ metabolites. The known synthetic processes for the metabolites of the $D_3$-series (especially as far as they relate to the preparation of side chain hydroxylated compounds) are, of course, in general not suitable for the preparation of the corresponding vitamin $D_2$ metabolites, since the latter are characterized by a side chain structure (i.e. presence of a double bond and an extra methyl group) which requires a different synthetic approach from that applicable to side chain hydroxylated $D_3$ compounds.

Two compounds structurally related to 25—OH—$D_2$ have been prepared, namely 22-dehydro-25-hydroxycholecalciferol, which may be considered a 24-desmethyl analog of 25—OH—$D_2$ (see U.S. Pat. No. 3,786,062), and 24,25-dihydroxyvitamin $D_2$, the 24-hydroxy-analog of 25—OH—$D_2$ [Jones et al. Biochemistry 18, 1094 (1979)]. However, the synthetic methods proposed in these reports are not applicable to the preparation of 25—OH—$D_2$ itself. No synthesis of the latter compound has appeared in the literature, and although there is the mention in the paper by Salmond et al. (Tetrahedron Letters, 1695-1698 (1977), see p. 1697 and footnote 11) of the successful preparation of 25—OH—$D_2$, no information on the overall process has been published to date.

DISCLOSURE OF INVENTION

A novel and convenient synthesis of 25-hydroxylated vitamin $D_2$ compounds has now been developed and is fully described herein. This synthesis provides 25-hydroxyvitamin $D_2$ (25—OH—$D_2$) and its 24-epimer, 25-hydroxy-24-epi-vitamin $D_2$ (25—OH—24-epi $D_2$), characterized by the structures shown below (where $X_1$ and $X_2$ are hydrogen and Y is methyl),

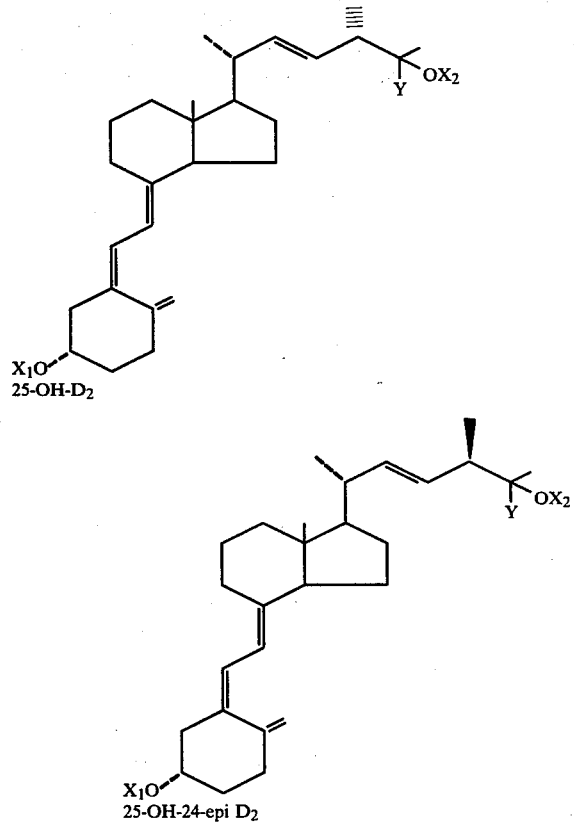

25-OH-$D_2$

25-OH-24-epi $D_2$ as well as the corresponding alkyl or aryl analogs, characterized by the structures above where Y is alkyl or aryl, and the hydroxy-protected derivatives of these compounds characterized by the structures above, where either of $X_1$ and $X_2$, or both of $X_1$ and $X_2$ are acyl.

In addition, the present process provides the 5,6-trans-isomers of the above compounds, and novel intermediates that are of utility for the preparation of 25—OH—$D_2$-analogs and/or isotopically-labeled products.

The term "acyl", as used in this specification or in the claims, signifies an aliphatic acyl group of from 1 to about 6 carbons, in all possible isomeric forms (e.g. formyl, acetyl, propionyl, butyryl, isobutyryl, valeryl, etc.), or an aromatic acyl group (aroyl group) such as benzoyl, the isomeric methyl-benzoyls, the isomeric nitro- or halo-benzoyls, etc., or a dicarboxylic acyl group of from 2 to 6 atoms chain length, i.e. acyl groups of the type ROOC(CH$_2$)$_n$CO—, or ROOCCH$_2$—O—CH$_2$CO—, where n has values between 0 and 4 inclusive and R is hydrogen or an alkyl radical, such as oxalyl, malonyl, succinoyl, glutaryl, adipyl, diglycolyl. The term "alkyl" refers to a lower alkyl group of 1 to 6 carbons in all possible isomeric forms, e.g. methyl, ethyl, propyl, isopropyl, butyl, isobutyl, sec.-butyl, pentyl, etc., and the word "aryl" signifies a phenyl or substituted phenyl group, e.g. alkylphenyl, methoxyphenyl, etc.

The overall process developed for the preparation of the above compounds may be divided into two general phases, namely (a) addition of a side chain fragment to a suitable steroidal precursor to produce a 5,7-diene steroid as the central intermediate, and (b) conversion of this 5,7-diene to the vitamin D structure with, as required, further modification of the side chain to produce the desired 25-hydroxylated compounds. This general scheme allows for some flexibility in the choice of specific starting material and in the exact order of individual process steps, two features that are of considerable practical advantage and convenience.

The reaction sequence illustrated by Process Scheme I presents an embodiment of the overall process, whereas Process Scheme II illustrates some of the options available for executing the last four steps of the synthesis.

Starting materials for the present process are steroidal 22-aldehydes in which the ring B double bond(s) is(are) protected in an appropriate manner. As shown in Process Scheme I, suitable compounds are for example, the PTAD-diene-protected-22-aldehyde (1) (where PTAD refers to the phenyltriazoline-3,5-dione-protecting group shown) or the 3,5-cyclo-22-aldehyde (4) wherein the $\Delta^5$-double bond is protected via i-ether formation. Both of these compounds are known products (see for example Barton et al. J. Chem. Soc.

Process Scheme I

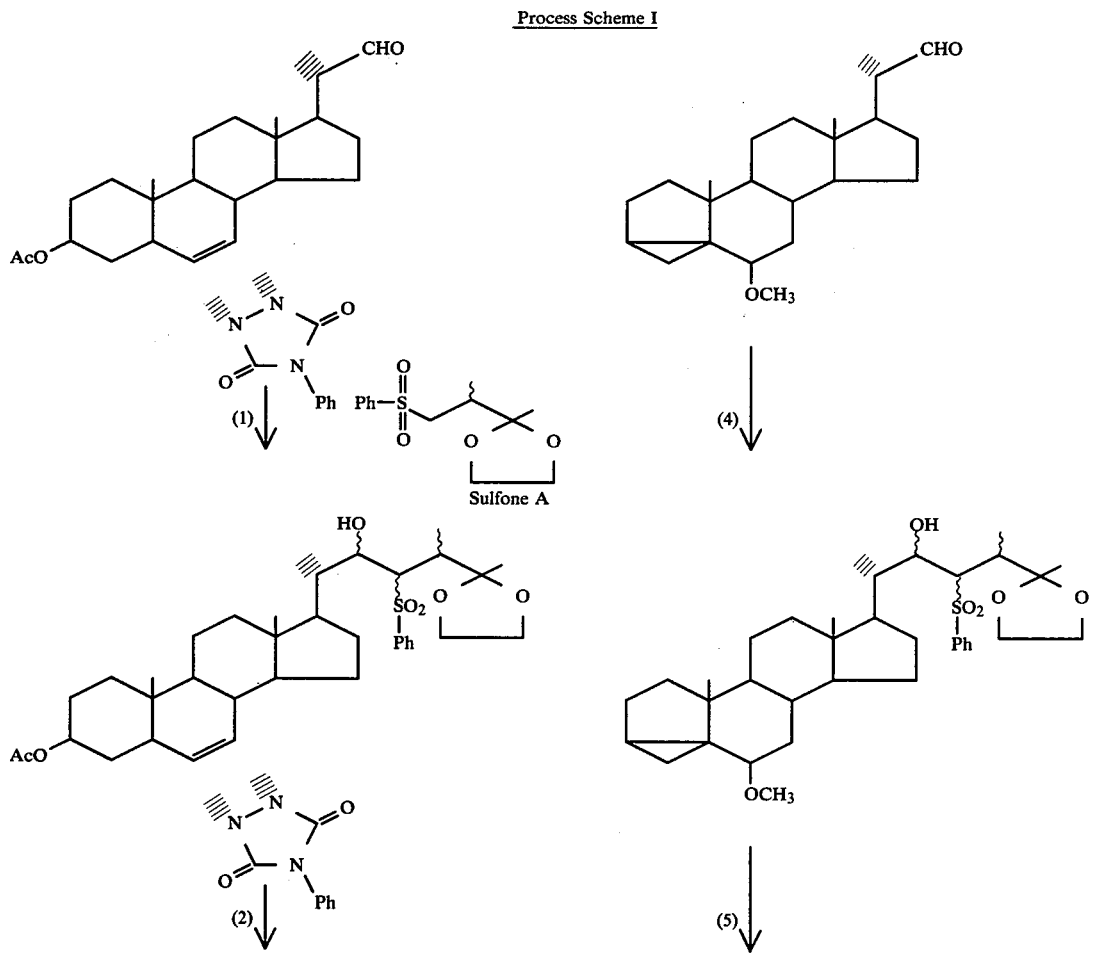

-continued
Process Scheme I
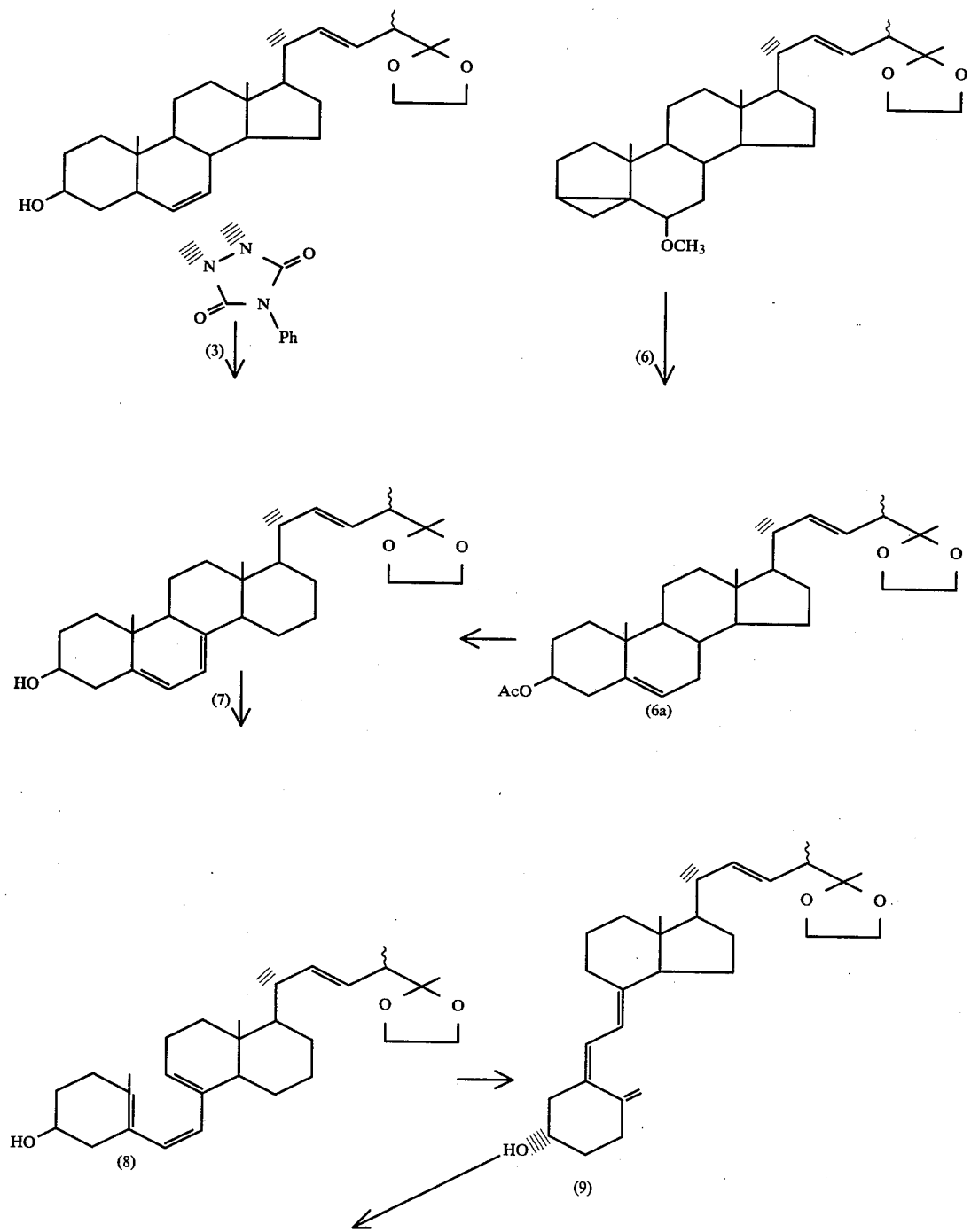

-continued
Process Scheme I

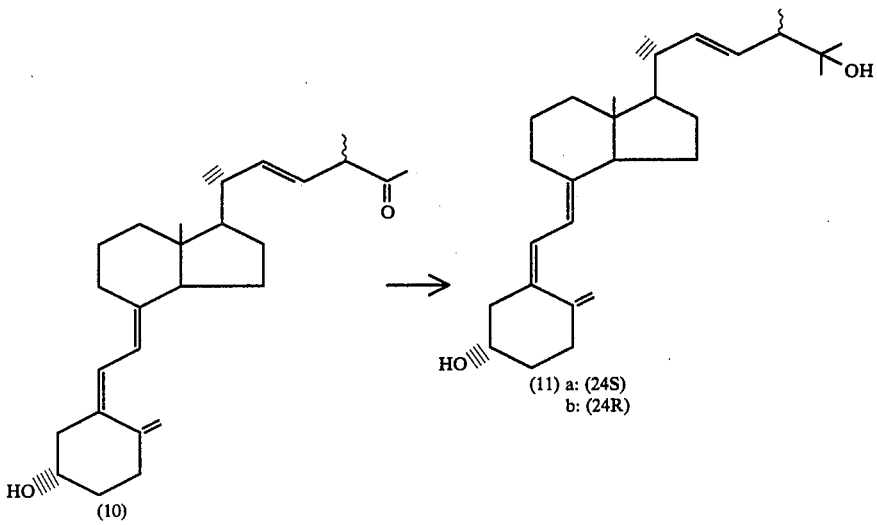

(11) a: (24S)
b: (24R)

(C) 1968 (1971); and Heyl et al. U.S. Pat. No. 2,623,052) and both can be carried through the steps of the present process in a basically analogous fashion.

The first step of this process comprises the addition of a suitable side chain fragment. Thus, condensation of aldehyde (1) with a sulfonyl-side chain fragment as shown in the Scheme (sulfone A, further described below) present in the form of its anion, in an ether or hydrocarbon solvent, provides the hydroxy-sulfone intermediate (2). The anion of the sulfone A side chain fragment is generated by treatment of the sulfone with a strong base, such as lithium diethylamide, n-butyl lithium or ethyl magnesium bromide (or similar Grignard reagent) in an ether or hydrocarbon solvent, and to this solution of sulfone anion the steroid aldehyde (compound 1) as an ether or hydrocarbon solution is then added. The reaction may be conducted advantageously at about room temperature, and is best effected under an inert atmosphere.

The analogous addition of sulfone A to aldehyde (4) provides the hydroxy-sulfone intermediate characterized by structure (5) in Process Scheme I.

The next step comprises the removal of the hydroxy- and phenylsulfonyl groups in the side chain with formation of the 22(23)-trans-double bond. Thus, treatment of compound (2), in methanol solution saturated with NaHPO$_4$, with sodium amalgam under an inert atmosphere, gives compound (3) featuring the desired trans-22-double bond in the side chain. The analogous treatment of compound (5) gives the 22-olefinic compound (6). If desired, the 22-hydroxy group in compounds (2) or (5) can also be acylated or sulfonylated (e.g. mesylated) prior to the Na/Hg-reduction step, but this is not generally required.

It is to be noted that, as shown in Process Scheme I, addition of the side chain fragment, sulfone A, to the aldehydes (1) or (4), does not cause epimerization at the asymetric center of carbon 20, i.e. the stereochemistry at that center is retained, as is required. If desired, retention of stereochemistry at carbon 20 may be checked at this stage of the synthesis by the conversion of intermediates of type (3) or (6) back to the original aldehyde starting materials. For example, subjecting compound (6) to ozonolysis with reductive work-up, using fully conventional and standard conditions, yields the corresponding C-22-aldehyde, i.e. the aldehyde of structure (4). Spectroscopic and chromatographic comparision of the aldehyde obtained from ozonolysis with the original starting material confirms retention of C-20 stereochemistry.

The third operation of the process involves conversion of these ring B-protected steroids to the desired 5,7-diene intermediate (7). In the case of the PTAD-diene-protected compound (3), this conversion is accomplished in a single step, namely treatment of (3) with a strong hydride reducing agent (e.g. LiAlH$_4$) in an ether solvent at reflux temperature gives the diene (7). This same material, compound (7), is produced from the i-ether derivative (6), in several steps, all of which are conventional and well-known in the art. The i-ether (6) is first solvolyzed in glacial acetic acid at reflux for ca. 2 hours to yield the corresponding 5-ene-3-acetate derivative (6a). This compound, in a hydrocarbon solution (e.g. hexane) at reflux temperature preferably under an inert atmosphere, is then treated with a brominating reagent (e.g. 1,3-dibromo-5,5-dimethylhydantoin) over a period of about 20 minutes, and the resulting C-7-bromo-intermediate is directly dehydrobrominated by dissolution in xylene and treatment with a base (e.g. s-collidine) at reflux temperatures under an inert atmosphere for about 90 minutes. The resulting product, the 5,7-diene-3-acetate is then isolated in the usual way and purified by high performance liquid chromatography or thin layer chromatography on silica gel plates. Simple hydrolysis of the acetate (5% KOH in MeOH) then provides 5,7-diene (7). This hydrolysis step may, however, also be omitted since both the 5,7-diene-3-ol (7) or the corresponding 3-O-acylates can be used for the subsequent steps of the process. Any such 3-O-acylates are, of course, also readily accessible by simple acylation of (7) according to conventional procedures.

Conversion of 5,7-diene (7) to the final vitamin D products comprises a sequence of four steps, the precise order of which may be altered as convenient. The sequence shown in Process Scheme I involves first the irradiation of an ether or hydrocarbon solution of the 5,7-diene (7) with ultraviolet light to yield the previtamin analog (8) which by warming (50°–90° C.) in a suitable solvent (e.g. ethanol, hexane) undergoes isomerization to the vitamin $D_2$-analog (9). The next step, removal of the ketal protecting group, is a critical one, since ketal removal by hydrolysis to give the corresponding keto-derivative (10) must be accomplished without isomerization of the 22(23)-double bond to the conjugated 23(24)-position. Isomerization of a $\beta,\delta$-unsaturated ketone to the conjugated $\alpha,\beta$-unsaturated ketone can readily occur under conditions of ketal hydrolysis, but must be avoided in this case, since it would defeat the purpose of the entire synthetic sequence. In the present process, ketal removal is achieved by heating ketal (9) in hydroxylic solvent under acid catalysis for 1-2 hours. (It is desirable to monitor the progess of reaction by periodic chromatographic analysis of the crude reaction mixture. Analysis by HPLC is suitable and convenient.) The product, ketone (10) thereby obtained, is then alkylated in the final step by means of a Grignard reagent (an alkyl-, or aryl-magnesium halide, e.g. methyl magnesium bromide in this case) to give the 25-hydroxyvitamin $D_2$ compound (11). Alkylation via an alkyllithium reagent, e.g. methyl lithium, is also effective and convenient. If the side chain fragment, sulfone A, as used in the first step, is racemic, i.e. exists as a mixture of its (R) and (S)-enantiomers, then compound (11) will be obtained as a mixture of two C-25-epimers, i.e. (24S)-epimer (11a) which corresponds to the natural product, and the (24R)-epimer (11b) which is 25—OH—24-epi-$D_2$. These C-24-epimers are conveniently separated by high performance liquid chromatography (HPLC) on an efficient microparticulate silica gel column to obtain 25—OH—$D_2$ (11a) and 25—OH—24-epi-$D_2$ (11b) in pure form.

It is to be noted that with racemic sulfone A as the side chain starting material, the early synthetic intermediates, e.g. (3) [or (6), and (6a)] as well as the 5,7-diene (7) and subsequent intermediates (8), (9), and (10) also occur as the two C-24-epimers. If desired and convenient, separation of epimers can be conducted at any of these intermediate stages, and the (24R) and (24S) epimers may then be processed separately through the remaining steps to yield 25—OH—$D_2$ (11a) or 25—OH—24-epi-$D_2$ (11b) as desired. It is generally convenient to effect separation at the stage of the final products.

Since the mixtures of (24R)- and (24S)-epimers arise when the side chain fragment, sulfone A, as used in the above process is itself a racemic compound, i.e. is present as an enantiomeric mixture of the (R) and (S) forms, it is also possible, if desired, to circumvent the need for epimer separation by the use of optically active sulfone A. Thus, use of the (R)-epimer of sulfone A in the present process yields specifically 25—OH—$D_2$ (11a), while use of the corresponding (S)-epimer of sulfone A provides 25—OH—24-epi-$D_2$ (11b) as well as, of course, the respective intermediates in the pure (24R) or (24S) forms; the use of such optically pure sulfone starting material requires no other modification of the process steps described.

It is also important to note that the exact sequence of steps between the 5,7-diene (7) and the final products may be altered. Indeed, there are three convenient synthetic sequences, all involving the same steps, but in different order. These alternate sequences are shown in Process Scheme II, where $X_1$ and $X_2$ in the structural drawings signify hydrogen or an acyl group such as for example acetyl, propionyl, butyryl, benzoyl or substituted benzoyl.

The first sequence (identified by the letter A in Process Scheme II), leading from diene (7A) (which, when $X_1$=H, corresponds to diene (7) of Process Scheme I) to intermediates (8A), (9A), and to the final product (11) presents the order of reactions as discussed above.

Alternatively, the ketal in diene (7A) may be hydrolyzed first (see sequence B in Process Scheme II), to yield the diene-ketone identified as (7B) in the scheme, which after irradiation gives the previtamin ketone (8B), and thermal isomerization then leads to vitamin $D_2$-ketone (10), which via a final Grignard reaction yields the 25—OH—$D_2$-epimers (11).

In the third sequence (C), the 5,7-diene-ketone (7B) is first reacted with Grignard reagent to yield the 25-hydroxy intermediate (7C), which after irradiation gives the corresponding 25—OH-previtamin $D_2$ (8C), and a final thermal isomerization provides the 25—OH—$D_2$ products (11).

Thus, these three sequences differ only in the exact order in which specific steps are carried out, but the experimental conditions for the individual steps are analogous to the procedures described earlier, and as described in detail by the Examples. Among the three alternate sequences, sequence A is generally preferred, because of the utility of intermediates such as (9A) and (10) for the preparation of other vitamin $D_2$-analogs and/or labeled derivatives (see also below).

For any of these sequences, the 5,7-diene (7) may be used as the free hydroxy compound or as its C-3-acylate. Depending on the subsequent reaction sequence, the final 25—OH—$D_2$ products will be obtained as the free hydroxy

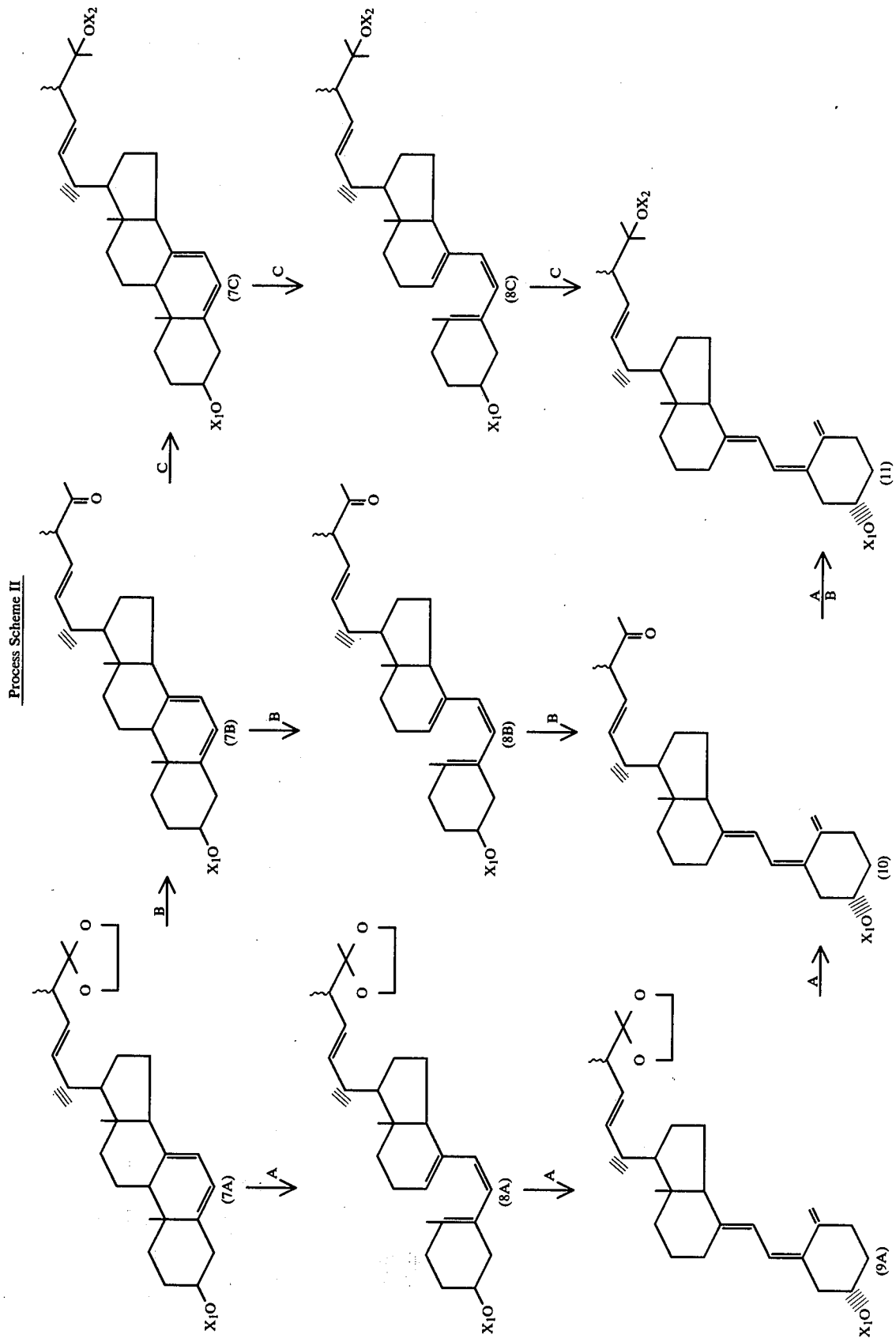

Process Scheme III

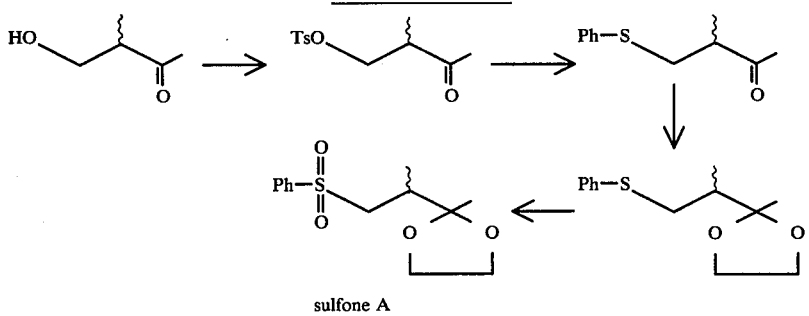

sulfone A compounds or, if desired, as the C-3-, or C-25-acylates, or 3,25-diacylates. Thus, synthesis according to sequence A or B would normally provide the 25—O—H—$D_2$ products as the free hydroxy compounds since the final Grignard reaction common to both sequences removes any acyl groups. Sequence C can be used to produce the 25—OH—$D_2$ epimers (11) as the free hydroxy compounds, or as the 3- or 25-monoacylate, or 3,25-diacylate, depending on the intermediate used. For example, the 5,7-diene intermediate (7C) shown in Process Scheme II, may be used as the 3-acyl, or 25-acyl, or 3,25-diacyl derivatives, which are available from the 3,25-diol by reaction with acyl chloride or acid anhydride reagents according to conventional procedures. Thus, reaction of 3,25-diol intermediate (7C) with acetic anhydride is pyridine at room temperature gives the 3-acetate, and the corresponding 3,25-diacetate is obtained by further acylation at elevated temperature; the latter may be selectively hydrolyzed with dilute KOH/MeOH at room temperature to give the 25-mono-acetate. Further conversion of any of such acyl intermediates through the remaining steps [to (8C) and (11)] in Process Scheme II, then yields the 25—OH—$D_2$-epimers (11) in any desired acylated form.

The individual 25—OH—$D_2$-epimers, 25—OH—$D_2$ (11a) or 25—OH—24-epi-$D_2$ (11b) when obtained in the free hydroxy forms, are also conveniently acylated at the C-3 or C-25, or at both positions, by reaction with acid anhydrides or acyl chlorides using conventional conditions. Thus, 25—OH—$D_2$ (11a) may be acylated to yield, for example, the 25—OH—$D_2$-3-acetate, or the corresponding 3,25-diacetate. The 3-monoacetate, in a like fashion, may be further acylated at C-25 by treatment with a different acylating reagent, or, alternatively, the 3,25-diacetate may be selectively hydrolyzed by mild base (KOH/MeOH) to give the 25-monoacetate, which if desired can be reacylated with a different acyl group at C-3. In addition to acetic anhydride, suitable acylating agents are propionic, butyric, pentanoic or hexanoic anhydrides or the corresponding acid chlorides, or aromatic acylating agents such as the acid chlorides of benzoic or substituted benzoic acids, or the anhydrides of dicarboxylic acids, such as succinic, glutaric, adipic, diglycolic anhydrides, or the acyl chlorides of these dicarboxylic acid monoesters.

In addition to the acylates, the 5,6-trans-isomers of 25—OH—$D_2$ and 25—OH—24-epi-$D_2$ are compounds of potential utility in medical applications because of their considerable vitamin D-like activity. These 5,6-trans-compounds are prepared from the 5,6-cis-isomers (i.e. 11a or 11b) by iodine catalyzed isomerization according to the procedures of Verloop et al. Rec. Trav. Chim. Pays Bas 78, 1004 (1969), and the corresponding 3- and/or 25-acylates are likewise obtained by analogous isomerization of the corresponding 5,6-cis-acylates, or by acylation of the 5,6-trans-25—OH—D compounds.

It is to be noted also that the 25-keto-intermediate (i.e. compound (10) in Process Scheme I) can serve as a substrate for the convenient preparation of 25—O—H—$D_2$ or its 24-epimer in isotopically labeled form, namely by reaction of the ketone with commercially available isotopically labeled Grignard or methyl lithium reagents to provide 25—OH—$D_2$ compounds labeled at carbon 26 with $^{13}C$, $^{14}C$, $^2H$ or $^3H$.

Furthermore, the keto-vitamin D compound (10) also serves as a convenient intermediate for the synthesis of 25—OH—$D_2$-analogs, of the formula (12) shown below,

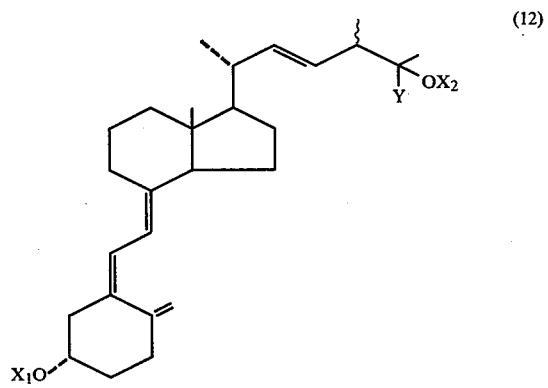

(12)

where $X_1$ and $X_2$ are selected from hydrogen and acyl, and where Y is an alkyl group other than methyl or an aryl group. These compounds are prepared by reaction of ketone (10) with the appropriate alkyl- or aryl-Grignard or alkyl- or aryl-lithium reagent. For example, treatment of ketone (10) with ethyl magnesium iodide yields product (12) above, where $X_1=X_2=H$, and Y=ethyl; likewise treatment of ketone (10) with isopropyl magnesium bromide, or phenyl magnesium bromide yields the corresponding 25—OH—$D_2$-congeners of structure (12) above, where Y=isopropyl, or phenyl, respectively, and other alkyl analogs of structure (12), e.g. where Y is propyl, butyl, sec.-butyl, isobutyl, pentyl, are prepared by analogous reactions. Acylation of these products by the procedures discussed above provides the C-3-, or C-25-O-acylates, or 3,25-di-O-acylates, and isomerization of the 5,6-double bond according to the procedure of Verloop et al. cited above yields the 5,6-trans-isomers of the compounds of structure (12) and/or the acylates thereof.

Since the compounds, where Y is a higher homolog of methyl, are generally more lipophilic, the alkyl- or aryl-analogues represented by structure (12) above or their 5,6-trans-isomers, are expected to have utility in applications where a greater degree of lipophilicity is desired.

The required side chain fragment, sulfone A, is itself prepared according to the process shown in Process Scheme III. This synthesis is straightforward and involves as a first step the reaction of commercially available 4-hydroxy-3-methylbutan-2-one with p-toluenesulfonylchloride to form the corresponding toluenesulfonyl ester. This product is then treated with thiophenol in the presence of base (e.g. potassium t-butylate) whereby the toluenesulfonyl group is displaced and the corresponding phenylthioether is formed. In the next step, the ketone group is protected as the ethylene ketal by reaction with ethylene glycol under acid catalysis, using conventional conditions well established in the art. Oxidation of this product with a peracid (e.g. perbenzoic acid, or m-chloroperbenzoid acid) in halocarbon solution (e.g. $CH_2Cl_2$) then provides the desired sulfone, labeled sulfone A, as shown in Process Scheme III.

If sulfone A is desired in optically active form, i.e. as the pure (R) or (S)-epimer, it is appropriate to use optically active starting materials, for example, the ethylene ketal of (3R)-4-hydroxy-3-methylbutan-2-one or the ethylene ketal of (3S-4-hydroxy-3-methylbutan-2-one. Each of these ethylene ketals is then processed through the appropriate steps of Process Scheme III, namely (a) tosylation, (b) phenylsulfide formation, and (c) peracid oxidation, to yield from the (R) ketal starting material the (S)-enantiomer of sulfone A, and from the (S)-ketal the (R)-enantiomer of sulfone A. The (R) and (S) ketal starting materials are themselves conveniently obtained from commercially available recemic α-methylacetoacetate ethyl ester (ethyl 2-methyl-3-oxobutanoate) as follows: The keto ester is converted to the ethylene ketal ester by reaction with ethylene glycol under acid catalysis using conventional procedures, and the ester function is then reduced ($LiAlH_4$ in ether) to yield the racemic ketal-alcohol (2,2-ethylenedioxy-3-methylbutan-4-ol). Resolution of the racemic mixture is accomplished by conversion to a mixture of diastereomers (by reaction of the alcohol function with an optically active acylating agent) which are then separated. For example, the alcohol can be converted to the corresponding α-methoxy-α-trifluoromethylphenylacetyl derivative (or similar optically active acylate) by reaction in pyridine solution with the chloride of optically active (+) α-methoxy-α-trifluoromethylphenylacetic acid (according to the procedures of, for example, Dale et al., J. Org. Chem. 34, 2543 (1961); Eguchi et al., Proc. Natl. Acad. Sci. USA 78, 6579 (1981)); this disastereomeric acyl-derivative mixture is now separable by HPLC or similar chromatographic methods into its two components, namely the acylate of the (R)-enantiomer and the acylate of the (S)-enantiomer. Removal of the acyl group in each compound by base hydrolysis under standard conditions then provides the ethylene ketal of (3R)-4-hydroxy-3-methylbutan-2-one, and the ethylene ketal of (3S)-4-hydroxy-3-methylbutan-2-one, which are then separately processed to the respective sulfone A enantiomer as described above. If desired, optically active hydroxybutanone intermediates, i.e. (3R)-4-hydroxy-3-methylbutan-2-one and (3S)-4-hydroxy-3-methylbutan-2-one, can also be prepared from naturally occurring optically active substrates. Thus, by reaction of the known (S)-3-hydroxy-2-methylpropanoic acid (β-hydroxyisobutyric acid) with methyl lithium there is obtained (3S)-4-hydroxy-3-methylbutan-2-one; and the corresponding (3R)-hydroxybutanone can be prepared from the same (S)-hydroxy-isobutyric acid, by transposition of functionalities, i.e. elaboration of the hydroxymethyl group to a methyl ketone function, and reduction of the acid to alcohol, according to obvious and conventional procedures.

The present invention is further described by means of the following illustrative examples. In these examples, numerals designating specific products (e.g. compounds (1), (2), (3) etc. in Examples 1 through 12, or compounds (7A), (8B), (8C), etc. in Examples 13 and 14) refer to the structures so numbered in Process Schemes I or II.

EXAMPLE 1

The C-22 aldehyde (1) is obtained by degradation or ergosterol acetate (in which the ring B diene system has been protected by Diels-Alder addition of 4-phenyl-1,2,4-triazoline-3,5-dione) according to the procedure of Barton et al. (supra). The i-ether aldehyde (4) is obtained from stigmasterol by the method of U.S. Pat. No. 2,623,052.

EXAMPLE 2

Synthesis of the Side Chain Fragment (Sulfone A)

To a stirred solution of 4-hydroxy-3-methylbutan-2-one (12.75 g; 0.125 mol) in pyridine (100 ml) is added p-toluenesulfonyl chloride (p-TsCl) (33.25 g, 0.175 mol) in portions, and after standing for 14 h at room temperature, the reaction mixture is poured into water and extracted with $CH_2Cl_2$. The extract is washed several times with aqueous $CuSO_4$ solution and water and then dried over anhydrous sodium sulfate. Removal of solvent under reduced pressure gives the crude tosylate which is used directly for the next reaction.

Thiophenol (14 g) dissolved in DMF (100 ml) is treated with t-BuOK (14 g). To this reagent, the tosylate is added and after 12 h at room temperature, the reaction mixture is poured into water and extracted with $CH_2Cl_2$. The extract is washed with aqueous $Na_2CO_3$ solution and water, then dried. Evaporation of solvent gives an oily residue which is purified by silica gel column chromatography. Pure phenyl sulfide is eluted with benzene (yield 15 g).

To this phenyl sulfide derivative (15 g), in benzene (100 ml), ethylene glycol (6 g) and p-TsOH (20 mg) is added and the reaction mixture is heated under a Dean-Stark trap for 3 h. After cooling, it is extracted with $Na_2CO_3$ solution and water, then dried and the solvent is evaporated. The product, the desired ketal, is chromatographically homogenous and can be used in the next step without further purification.

Crude ketal in dichloromethane (250 ml) solution is treated with m-chloroperbenzoic acid (m-CPBA) (80–85%, 27 g, added in portions) while maintaining the temperature of the reaction mixture below 30° C. After the addition of reagent, the reaction is allowed to stand at room temperature with occasional shaking. When the reaction reaches completion (about 1.5 h), the aromatic acids are removed by extraction with aqueous $NH_3$, and the organic layer is washed with water and dried. Evaporation of solvent gives the oily sulfone (sulfone A) in essentially quantitative yield (19 g). The product is substantially pure (homogenous by TLC) and can be used without any further purification; $^1$H-NMR; δ; 1.18 (d, J=7 Hz, 3H, C$\underline{H}_3$—CH—), 1.19 (s, 3H, C$\underline{H}_3$—C—), 3.84 (m, 4H, ketal-$\underline{H}$), 7.3–7.6 and 7.6–7.9 (m, 3H+2H, aromatic protons); IR, $\nu_{max}^{KBr}$: 1305,1147,1082 cm$^{-1}$; mass spectrum, m/z (rel. intensity): 255 (M$^+$-Me, 21), 184 (66), 87 (92), 43 (100).

EXAMPLE 3

Coupling of Sulfone A to Aldehyde (1): Hydroxysulfone (2) and Olefin (3)

Grignard reagent is prepared from Mg (535 mg; 22.22 mmol) and ethyl bromide in ether (10 ml), and the vigorously stirred solution is treated with sulfone A (6 g; 2.22 mmol) in benzene (6 ml). The precipitate formed is ground with a spatula, stirring is continued, and after 15 min the aldehyde (1) (2.0 g) is added in benzene (10 ml). The reaction mixture is stirred at room temperature for 24 h, then poured into aqueous (NH$_4$)$_2$SO$_4$ solution and extracted with benzene. The organic layer, after washing with water, drying and evaporation gives an oily residue which is chromatographed on silica gel. In the benzene-ether fractions (8:2), excess sulfone is recovered (4.5 g); elution with benzene-ether (3:1) affords unreacted aldehyde (1) (1.0 g); the reaction products (2) are eluted with ethyl acetate.

The crude mixture of steroidal α-hydroxysulfones (2) is dissolved in methanol (200 ml) saturated with Na$_2$HPO$_4$. Sodium amalgam (5.65%, 15 g) is added and the reaction mixture is stirred at 4° C. for 15 h.

After completion of the Na/Hg reduction, mercury is removed by filtration, and methanol by evaporation under reduced pressure, water is added and the organic material is extracted with benzene. After drying and evaporation of solvent, the oily residue is chromatographed on a silica gel column. Elution with benzene-ether (1:4) gives compound (3) a colorless foam; $^1$H-NMR, δ: 0.80 (s, 18-$\underline{H}$), 0.97 (s, 19-$\underline{H}$), 1.22 (s, 26-$\underline{H}$), 3.93 (m, 4H, ketal-H), 4.44 (m, 1H, 3α-$\underline{H}$), 5.25–5.45 (m, 2H, 22-H and 23-$\underline{H}$), 6.23 and 6.39 (doublets, J=8 Hz, 2×1H, 7-$\underline{H}$ and 6-$\underline{H}$), 7.25–7.45 (m, 5H, —C$_6$H$_5$); IR, $\nu_{max}^{CHCl_3}$: 3603 (O-H), 1749, 1692 (C=O), 1406,1038 cm$^{-1}$; mass spectrum, m/z: 440 (M$^+$-triazoline, 24), 87 (100).

(To increase yield, unreacted aldehyde (1),as recovered above, can be recycled through the sulfone addition, and the resulting α-hydroxy sulfones (2) are then, as above, treated with sodium amalgam in buffered methanol to provide additional olefin (3). The above reactions are preferably conducted under an inert atmosphere, such as argon.)

EXAMPLE 4

Coupling of Sulfone A to Aldehyde (4): Hydroxysulfone (5) and Olefin (6)

Grignard reagent is prepared from Mg (75 mg, 3.1 mmol) and ethyl bromide in ether (10 ml). To the stirred solution of ethyl magnesium bromide, sulfone A (891 mg; 3.3 mmol) in benzene (5 ml) is added. After stirring the resulting suspension at room temperature for 15 min, a solution of aldehyde (4) (290 mg) in benzene (5 ml) is added. The reaction is continued for 2.5 h, then quenched with saturated (NH$_4$)$_2$SO$_4$ solution (5 ml) and diluted with ether. The separated organic layer is washed with water, dried, and evaporated. The oily residue containing (5) is treated with acetic anhydride (2 ml) and pyridine (2 ml). The reaction mixture is allowed to stand for 24 h, poured into water and extracted with benzene. The benzene extract is washed with an aqueous solution of CuSO$_4$, water, dried, and evaporated. The crude product [the acetate of (5)] is dissolved in methanol saturated with Na$_2$HPO$_4$ and sodium amalgam (5.65%, 8 g) is added. The reaction mixture is stirred at 4° C. for 16 h. After the reaction, mercury is removed by filtration, methanol is evaporated, and water and benzene are added to dissolve the residue. The benzene layer is dried and evaporated. The oily residue is chromatographed over silica gel. Elution with benzene-ether mixture (93:7) affords compound (6) (206 mg; 54%), $^1$H-NMR, δ: 0.74 (s, 18-$\underline{H}$), 1.04 (s, 19-$\underline{H}$), 1.25 (s, 26-H), 2.78 (m, 1H, 6α-$\underline{H}$), 3.34 (s, 3H, —OC$\underline{H}_3$), 3.97 (m, 4H, ketal-H), 5.25–5.45 (m, 2H, 22-$\underline{H}$ and 23-$\underline{H}$), IR,$\nu_{max}^{KBr}$: 3470 (O-H), 1095 cm$^{-1}$; mass spectrum, m/z (rel. intensity): 456 (M$^+$, 1), 441 (M$^+$-Me, 45), 87 (100). It should be noted that the acetylation step described above is not essential and may be omitted if desired; i.e. the hydroxysulfone (5) may be submitted directly to Na/Hg-reduction, as in Example 3. The above reactions are preferably conducted uner an inert atmosphere, e.g. argon.

EXAMPLE 5

Removal of PTAD-protecting Group: 5,7-Diene (7)

A mixture of the compound (3) (1 g) and lithium aluminum hydride (1.8 g) in THF (120 ml) is heated under reflux for 10 h. After cooling, excess reagent is destroyed with a few drops of water, and the mixture is dried over anhydrous MgSO$_4$, filtered, and solvent is evaporated to give colorless crystalline material. Crude diene 7 is repeatedly crystallized from ethanol; first and second crops combined give 415 mg of (7). The mother liquor is chromatographed on silica gel column, to give with benzene-ether (7:3), an additional 120 mg of (7); total yield 535 mg (79%); m.p. 132°–134° C. (from ethanol), $^1$H-NMR, δ: 0.63 (s, 18-$\underline{H}$), 0.95 (s, 19-$\underline{H}$), 1.23 (s, 26-$\underline{H}$), 3.63 (m, 1H, 3α-$\underline{H}$), 3.95 (m, 4H, ketal-H), 5.20–5.50 (m, 3H, 22-H, 23-$\underline{H}$ and 7-$\underline{H}$), 5.57 (m, 1H, 6-H); IR,$\nu_{max}^{KBr}$: 3430 (O-H), 1063, 1038 cm$^{-1}$; mass spectrum, m/z (rel. int.): 440 (M$^+$, 50), 407 (M$^+$—H$_2$O—Me, 11), 87 (100); UV, $\lambda_{max}^{EtOH}$: 282 nm (ε=11,000).

EXAMPLE 6

Irradiation of Compound (7): Previtamine Analog (8)

A solution of diene (7) (50 mg) in 150 ml of benzene-ether (1:4) is cooled on ice and deoxygenated with argon for 20 min. The reaction mixture is irradiated under argon atmosphere for 18 min with a mercury arc lamp (Hanovia SA-1) fitted with a Vycor filter. The solvent is evaporated and the residue is chromatographed on HPLC (6.2 L mm×25 cm microparticulate silica gel, 4 ml/min, 1400 psi) and eluted with 2% 2-propanol in hexane to yield 22 mg (44%) of previtamin (8); $^1$H-NMR; δ: 0.73 (s, 18-H), 1.24 (s, 26-H), 1.64 (s, 19-$\underline{H}$), 3.96 (m, 5H, ketal-$\underline{H}$ and 3α-$\underline{H}$), 5.35 (m, 2H, 22-$\underline{H}$ and 23-$\underline{H}$), 5.50 (m, 1H, 9-$\underline{H}$), 5.69 and 5.94 (doublets, J=11.5 Hz, 2×1H, 6-$\underline{H}$ and 7-$\underline{H}$); UV, $\lambda_{max}^{EtOH}$: 263 nm (ε=8,900).

EXAMPLE 7

Isomerization of (8) to the Vitamin-Analog (9)

Previtamin 8 (22 mg) is dissolved in ethanol (40 ml) and heated under reflux for 150 min (argon atmosphere). The product is purified by HPLC to yield 18 mg (82%) of the pure vitamin (9); $^1$H-NMR, δ: 0.85 (s, 18-$\underline{H}$), 1.24 (s, 26-$\underline{H}$), 3.94 (m, 5H, ketal-$\underline{H}$ and 3α-$\underline{H}$), 4.81 and 5.04 (2 narrow m, 2×1H, 19(Z)- and 19(E)-$\underline{H}$), 5.33 (m, 2H, 22-$\underline{H}$ and 23-$\underline{H}$), 6.03 (d, J=11 Hz, 1H, 7-$\underline{H}$), 6.22 (d, J=11 Hz, 1H, 6-$\underline{H}$); mass spectrum, m/z (rel. int.): 440 (M$^+$, 17) 87 (100), UV, $\lambda_{max}^{EtOH}$: 265 nm (ε=17,000).

EXAMPLE 8

Hydrolysis of the ketal: Keto-Vitamin D$_2$-Analog (10)

To the solution of compound (9) (18 mg) in ethanol (35 ml), p-toluenesulfonic acid (7.5 mg) in water (1 ml) is added and the reaction mixture is heated under reflux for 90 min (the reaction course is monitored by HPLC). The solvent is evaporated, the residue is dissolved in benzene and extracted with water. The benzene solution is dried (anhydrous MgSO$_4$), and evaporated to yield product (10) (16 mg; 99%). $^1$H-NMR, δ: 0.57 (s, 18-$\underline{H}$), 1.04 (d, J=7 Hz, 21-$\underline{H}$), 1.13 (d, J=7 Hz, 28-$\underline{H}$), 2.12 (s, 3H, 26-$\underline{H}$), 3.10 (m, 1H, 24-$\underline{H}$), 3.96 (m, 1H, 3α-$\underline{H}$), 4.82 and 5.05 (2 narrow m, 2×1H, 19(Z)- and 19(E)-$\underline{H}$), 5.2–5.5 (m, 2H, 22-$\underline{H}$ and 23-$\underline{H}$), 6.03 (d, J=11.5 Hz, 1H, 7-$\underline{H}$), 6.22 (d, J=11.5 Hz, 1H, 6-$\underline{H}$), IR, $\nu_{max}^{CHCl_3}$: 3596 (O-H), 1709 cm$^{-1}$ (C=O); mass spectrum, m/z (rel. int.): 396 (M$^+$, 41), 363 (M$^+$—H$_2$O—Me), 13), 271 (M$^+$-side chain, 16), 253 (m$^+$-side chain-H$_2$O, 23), 136 (100), 118 (95); UV, $\lambda_{max}^{EtOH}$: 265 nm (ε=17,900).

EXAMPLE 9

Reaction of Ketone (10) with Methylmagnesium Iodide: 25—OH—D$_2$, (11a), and its Epimer (11b)

Grignard reagent is prepared from magnesium (240 mg) and methyl iodide in anhydrous ether (20 ml). To one-tenth of this solution (2 ml; 0.5 M solution of CH$_3$MgI) ketone (10) (16 mg; 0.04 mmol) in ether (2 ml) is added. The reaction mixture is stirred at room temperature for 2 h under an inert atmosphere, then quenched with squeous solution of NH$_4$Cl, diluted with benzene and washed with water. The organic layer is separated, dried and evaporated. The crude product is first purified by silica gel column chromatograhy (elution with 20% ether in benzene) and the mixture of (11a) and (11b) (16 mg; 96%) thereby obtained is then repeatedly chromatographed on HPLC column using 2% 2-propanol in hexane as an eluent to separate the 24-stereoisomers, 24-epi-25—OH—D$_2$ (11b) and 25—OH—D$_2$ (11a). Chromatography and rechromatography of each stereoisomer yields 4 mg of (11b) (collected at 68 ml), 4 mg of (11a) (collected at 74 ml) and 7 mg of the mixture of both epimers. Treatment of 2 mg of the epimer mixture with excess acetic anhydride in pyridine solution at room temperature overnight followed by standard work-up yields the corresponding 3-O-acetates.

25—OH—D$_2$ (11a): $[α]_D^{25}$+56.8° (C=0.2 in EtOH); $^1$H-NMR, δ: 0.57 (s, 18-$\underline{H}$), 1.00 (d, J=7 Hz, 28-$\underline{H}$), 1.04 (d, J=7 Hz, 21-$\underline{H}$), 1.15 and 1.17 (2 singlets, 26-$\underline{H}$ and 27-$\underline{H}$), 3.95 (m, 1H, 3α-$\underline{H}$), 4.82 and 5.05 (2 narrow m, 2×1H, 19(Z)- and 19(E)-H), 5.23–5.43 (m, 2H, 22-$\underline{H}$ and 23-$\underline{H}$), 6.05 and 6.22 (2 doublets, J=11 Hz, 2×1H, 7-$\underline{H}$ and 6-$\underline{H}$); IR, $\nu_{max}^{KBr}$: 3401 (O-H), 1645, 1631 (C=C), 971 cm$^{-1}$ (trans C=C); mass spectrum, m/z (rel. int.): 412 (M$^+$, 63), 394 (M$^+$—H$_2$O, 10), 379 (M$^+$—H$_2$O—Me, 23), 271 (M$^+$-side chain, 37), 253 (M$^+$-side chain-H$_2$O, 43), 136 (100), 118 (86), 59 (99), UV, $\lambda_{max}^{EtOH}$: 265 nm (ε=17,950).

24-epi-25—OH—D$_2$ (11b): $[α]_D^{25}$+50.7° (C=0.2 in EtOH), $^1$H-NMR, δ: 0.57 (s, 18-$\underline{H}$), 0.99 (d, J=7 Hz, 28-$\underline{H}$), 1.03 (d, J=7 Hz, 21-$\underline{H}$), 1.14 and 1.16 (2 singlets, 26-$\underline{H}$ and 27-$\underline{H}$), 3.94 (m, 1H, 3α-$\underline{H}$), 4.82 and 5.03 (2 narrow m, 2×1H, 19(Z)- and 19(E)-$\underline{H}$), 5.20–5.40 (m, 2H, 22-$\underline{H}$ and 23-$\underline{H}$), 6.04 and 6.22 (2 doublets, J=11 Hz, 2×1H, 7-$\underline{H}$ and 6-$\underline{H}$), IR, $\nu_{max}^{KBr}$: 3401 (OH), 1643, 1630 (C=C), 971 cm$^{-1}$ (trans C=C); mass spectrum, m/z (rel. int.): 412 (M$^+$, 62) 394 (M$^+$—H$_2$O; 12), 379 (M$^+$—H$_2$O—Me, 31), 271 (M$^+$-side chain, 44), 253 (M$^+$-side chain-H$_2$O, 55), 136 (100), 118 (67), 69 (38); UV, $\lambda_{max}^{EtOH}$: 265 nm (ε=17,300).

It should be noted that from pure provitamin (7) further synthesis (i.e. the irradiation, isomerization, deketalization and Grignard reaction steps) may be accomplished without chromatographic purification of any intermediate. Careful column chromatography on silica gel before the final separation on HPLC removes all by-products.

By reaction of 25—OH—D$_2$ (11a) with each of the following acylating reagents, acetic anhydride, propionic anhydride, benzoyl chloride and succinic anhydride, under conventional conditions, there is obtained, respectively:

25—OH—D$_2$-3-acetate
25—OH—D$_2$-3,25-diacetate
25—OH—D$_2$—3-propionate
25—OH—D$_2$-3,25-dipropionate
25—OH—D$_2$—3-benzoate
25—OH—D$_2$—3,25-dibenzoate
25—OH—D$_2$—3-hemisuccinate.

By reaction of 25—OH—24-epi-D$_2$ (11b) with, respectively, acetic anhydride, benzoyl chloride and diglycolic anhydride, tender conventional conditions, there is obtained, respectively:

25—OH—24-epi-D$_2$-3,25-diacetate
25—OH—24-epi-D$_2$-3-benzoate
25—OH—24-epi-D$_2$-3-hemidiglycolate.

EXAMPLE 10

By coupling of aldehyde (1) with optically active (R)-sulfone A having the structure

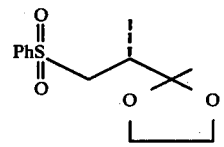

and subsequent Na/Hg reduction of the product according to the conditions of the experiment described in Example 3, there is obtained compound (3) having the (24S) configuration in the side chain as shown by the structure,

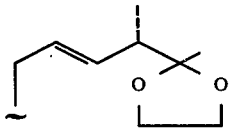

and treatment of this product with LiAlH$_4$ according to the conditions of Example 5 provides the 5,7-diene (7) having the (24S)-side chain configuration; by irradiation of this product and subsequent thermal isomerization according to the conditions of Examples 6 and 7 there are obtained, successively, the previtamin D compound (8) and vitamin D compound (9) having the (24S) configuration. Hydrolysis of compound (9) thus obtained, according to the conditions of Example 8, provides the (24S)-ketovitamin D compound (10) and from this product, by a Grignard reaction, according to Example 9 there is obtained 25—OH—D$_2$ (structure (11a) in Process Scheme I).

EXAMPLE 11

Using optically active (S)-sulfone A, having the structure

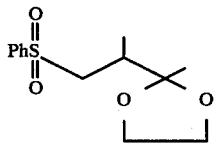

in the reactions described in Example 3, there is obtained compound (3), having the (24R)-side chain structure as shown below

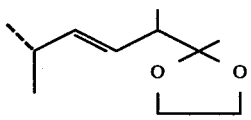

and reduction of this product according to the conditions of Example 5 provides the 5,7-diene (7) having the (24R) configuration. Irradiation of (24R)-(7) according to Example 6 gives the previtamin D analog (8) with the (24R) configuration, and by subsequent thermal isomerization, according to the conditions of Example 7, there is obtained the vitamin D compound (9) having the (24R)-side chain configuration. Ketal hydrolysis, according to the conditions of Example 8, then yields the (24R)-25-ketovitamin D (10), and by a reaction of this product with a methyl Grignard reagent according to the conditions of Example 9, there is obtained 25-hydroxy-24-epi-vitamin D$_2$ (structure 11b, in Process Scheme I).

EXAMPLE 12

Preparations of 5,6-trans-Compounds

25—OH—D$_2$ (compound 11a) is dissolved in ether containing a drop of pyridine and treated with a solution of iodine in hexane (ca. 0.5 mg/ml) for 15 min. Addition of an aqueous solution of sodium thiosulfate, separation of the organic phase, and evaporation of solvents yields a residue, from which the desired 25-hydroxy-5,6-trans-vitamin D$_2$ is isolated by HPLC using a microparticulate silica gel column and 2% of 2-propanol in hexane as eluent.

By the same procedure, there is obtained from 25-hydroxy-24-epi-D$_2$ the corresponding trans-isomer, namely 25-hydroxy-5,6-trans-24-epi-D$_2$.

From 25—OH—D$_2$ 3-acetate, there is obtained 25—OH—5,6-trans-D$_2$ 3-acetate, and from 25—O-H—24-epi-D$_2$ 3-acetate there is obtained 25—OH—5,6-trans-24-epi-D$_2$ 3-acetate by the application of the above isomerization procedure.

Acylation of 25—OH—5,6-trans-D$_2$ or 25—O-H—5,6-trans-24-epi-D$_2$ under conventional conditions provides the respective acylates, such as:
25—OH—5,6-trans-D$_2$-3-acetate
25—OH—5,6-trans-D$_2$-3,25-diacetate
25—OH—5,6-trans-D$_2$-3-benzoate
25—OH—5,6-trans-D$_2$-3-acetate-25-benzoate
25—OH—5,6-trans-24-epi-D$_2$-3-acetate
25—OH—5,6-trans-24-epi-D$_2$-3,25-dibenzoate.

EXAMPLE 13

Hydrolysis of 5,7-diene-25-ketal (compound (7A), where $X_1$=H) using the conditions described in Example 8 gives 3$\beta$-hydroxy-24-methyl 27-norcholesta-5,7,22-trien-25-one (compound 7B, where $X_1$=H). Irradiation of this product under conditions analogous to those of Example 6 gives 6 gives the 25-keto previtamin D$_2$ analog characterized by structure (8B), where $X_1$=H. Heating of (8B) in an ethanol solution according to the conditions of Example 7 provides the 25-keto vitamin D$_2$ product (compound 10, where $X_1$=H).

EXAMPLE 14

Reaction of 3$\beta$-hydroxy-24-methyl-27-norcholesta-5,7,22-trien-25-one (compound (7B), where $X_1$=H) as obtained in Example 13 with methyl magnesium bromide in accordance with the conditions of Example 9 gives 24-methylcholesta-5,7,22-triene-3$\beta$,25-diol (compound (7C), where $X_1$=$X_2$=H). Irradiation of this product, according to the conditions of Example 6, gives 25-hydroxy previtamin D$_2$ product characterized by structure (8C, where $X_1$=$X_2$=H). Thermal isomerization of this previtamin using the conditions of Example 7 provides the 25-hydroxyvitamin D$_2$ compound (11; where $X_1$=$X_2$=H).

Processing of 24-methylcholesta-5,7,22-triene-3$\beta$,25-diol 3,25-diacetate (compound 7C, $X_1$=$X_2$=acetyl) through the reaction steps involving irradiation and thermal isomerization according to the conditions of Examples 6 and 7 respectively gives the 25—OH—D$_2$ 3,25-diacetate epimers (compound (11), where $X_1$=$X_2$=acetyl).

EXAMPLE 15

Using the conditions analogous to those of Example 9, Mg is reacted with the following halides,
ethyl iodide; propyl iodide; isopropyl bromide; butyl bromide; sec.-butyl iodide; isobutyl iodide; pentyl iodide; and phenyl bromide,
to obtain the corresponding Grignard reagents.

By reaction of each of these reagents with ketone (10) by procedures analogous to that of Example 9, there are obtained, respectively, the following products:
compound (12) where $X_1$=$X_2$=H, Y=ethyl
compound (12) where $X_1$=$X_2$=H, Y=propyl
compound (12) where $X_1$=$X_2$=H, Y=isopropyl
compound (12) where $X_1$=$X_2$=H, Y=butyl
compound (12) where $X_1$=$X_2$=H, Y=sec.-butyl compound (12) where $X_1=X_2=H$, $Y=$isobutyl
compound (12) where $X_1=X_2=H$, $Y=$pentyl
compound (12) where $X_1=X_2=H$, $Y=$phenyl By reaction of ketone (10) with isotopically labeled methyl Grignard reagents, namely $^{13}CH_3MgI$, $^{14}CH_3MgI$, $C^2H_3MgI$, $C^3H_3MgI$, under conditions analogous to those of Example 9, there are obtained, respectively, the following products:

compound (12) where $Y=^{13}CH_3$, $X_1=X_2=H$
compound (12) where $Y=^{14}CH_3$, $X_1=X_2=H$
compound (12) where $Y=C^2H_3$, $X_1=X_3=H$
compound (12) where $Y=C^3H_3$, $X_1=X_2=H$ characterized by isotopic substitution in the methyl group of carbon 26 of the molecule.

We claim:

1. A process for preparing compounds having the formula

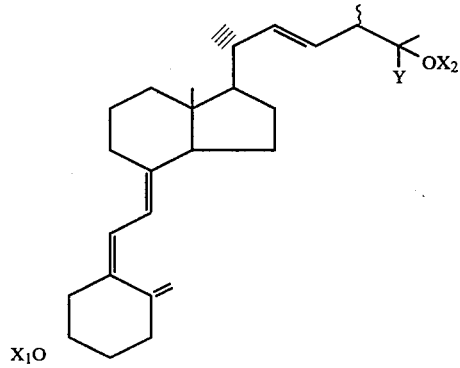

wherein $X_1$ and $X_2$ are each selected from hydrogen or acyl, and Y is an alkyl or aryl group, which comprises, irradiating a 5,7-diene steroid of the formula

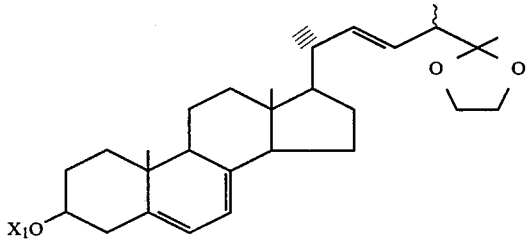

wherein $X_1$ is hydrogen or acyl, with ultraviolet light to obtain the corresponding previtamin D product, isomerizing said previtamin D compound in an inert solvent at a temperature from about room temperature to about 100° C. for a time sufficient to reach equilibrium, thereby obtaining a vitamin D compound of the formula

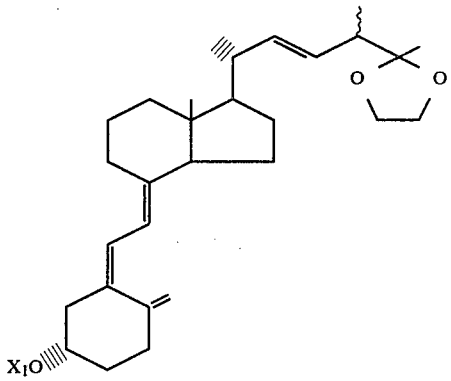

where $X_1$ is hydrogen or acyl, subjecting said vitamin D compound to acid catalyzed hydrolysis to remove the ketal protecting group thereby obtaining the corresponding ketone, subjecting said ketone to alkylation with a reagent of the formula YMg-halide or YLi, where Y is an alkyl or aryl group and the halide is chloride, bromide or iodide, and, optionally, acylating one or both free hydroxy groups.

2. The process of claim 1 wherein $X_1$ and $X_2$ are hydrogen and Y is methyl.

3. The process of claims 1 or 2 wherein the 5,7-diene steroid has the 24(R) configuration.

4. The process of claims 1 or 2 wherein the 5,7-diene steroid has the 24(S) configuration.

5. The process of claims 3 or 4, wherein the 5,7-diene steroid has the (24R) or the (24S) configuration.

6. Compounds having the formula

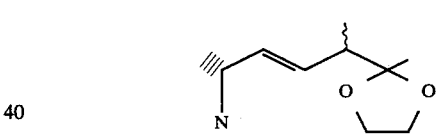

where N is a steroid nucleus selected from the group consisting of

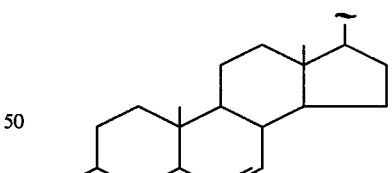

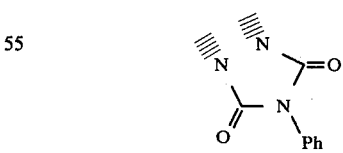

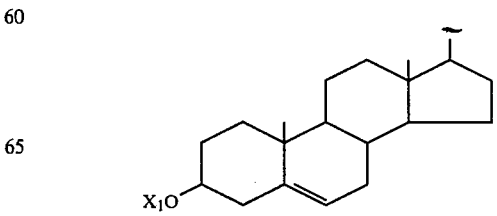

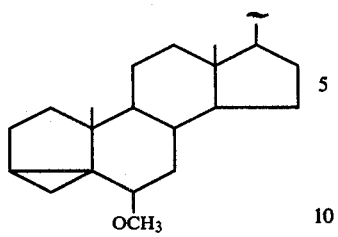

wherein $X_1$ is hydrogen or acyl.

7. The compounds of claim 6 wherein the asymetric center at carbon 24 has the (R) configuration.

8. The compounds of claim 6 wherein the asymetric center at carbon 24 has the (S) configuration.

9. Compounds having the formula

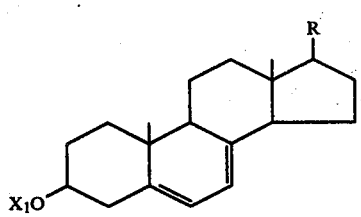

wherein $X_1$ is hydrogen or acyl, and R is selected from the group consisting of

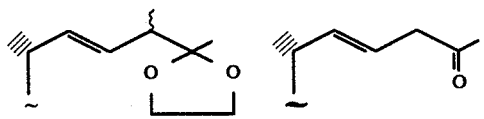

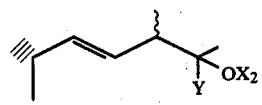

wherein $X_2$ is hydrogen or acyl, and Y is an alkyl or aryl group.

10. The compounds of claim 9 wherein $X_1$ and $X_2$ are hydrogen or acetyl and Y is methyl.

11. The compounds of claims 9 or 10 wherein the asymetric center at carbon 24 has the (R) configuration.

12. The compounds of claims 9 or 10 wherein the asymetric center at carbon 24 has the (S) configuration.

13. The compound having the formula

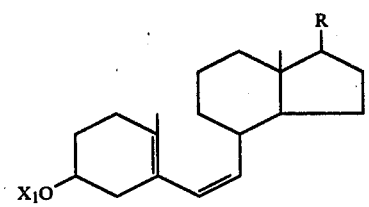

wherein $X_1$ is hydrogen or acyl, and where R is selected from the group consisting of

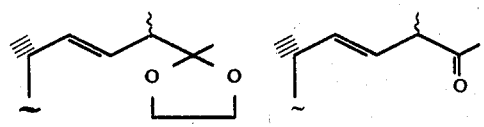

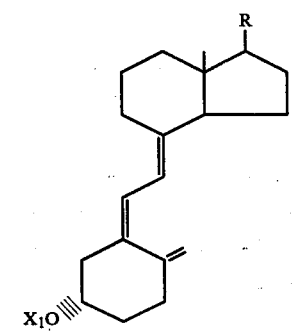

wherein $X_2$ is hydrogen or acyl and Y is an alkyl or aryl group.

14. The compounds of claim 13 wherein $X_1$ and $X_2$ are hydrogen or acetyl and Y is methyl.

15. The compounds of claims 13 or 14 wherein the asymetric center at carbon 24 has the (R) configuration.

16. The compounds of claims 13 or 14 wherein the asymetric center at carbon 24 has the (S) configuration.

17. Compounds having the formula

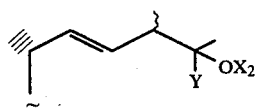

wherein $X_1$ is hydrogen or acyl, and where R is selected from the group consisting of

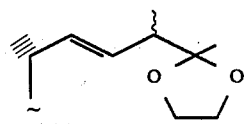

wherein $X_2$ is hydrogen or acyl and Y is alkyl or aryl, with the proviso that Y cannot be a $CH_3$ group.

18. The compounds of claim 17, wherein R is the group and $X_1$ is hydrogen, acetyl or benzoyl.

19. The compounds of claim 18 wherein the asymetric center at carbon 24 has the (R) configuration.

20. The compounds of claim 18 wherein the asymetric center at carbon 24 has the (S) configuration.

21. The compounds of claim 17 wherein R is the group

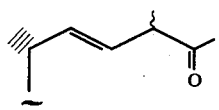

and $X_1$ is hydrogen, acetyl or benzoyl.

22. The compounds of claim 21 wherein the asymetric center at carbon 24 has the (R) configuration.

23. The compounds of claim 21 wherein the asymetric center at carbon 24 has the (S) configuration.

24. The compounds of claim 17 wherein R is the group

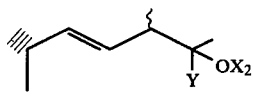

25. The compounds of claim 24 wherein $X_1$ is selected from the group consisting of acetyl, benzoyl, succinyl, and diglycolyl, and $X_2$ is selected from the group consisting of hydrogen, acetyl, benzoyl, succinyl and diglycolyl.

26. The compounds of claims 24 or 25 wherein the asymetric center at carbon 24 has the (R) configuration.

27. The compounds of claims 24 or 25 wherein the asymetric center at carbon 24 has the (S) configuration.

28. Compounds having the formula

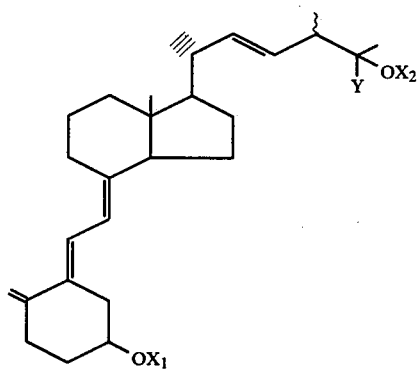

wherein $X_1$ and $X_2$, which may be the same or different, are hydrogen or acyl, and Y is an alkyl or aryl group with the proviso that Y cannot be a $CH_3$ group.

29. The compounds of claim 28 wherein the asymetric center at carbon 24 has the (R) configuration.

30. The compounds of claim 28 wherein the asymetric center at carbon 24 has the (S) configuration.

31. A process for preparing compounds having the formula

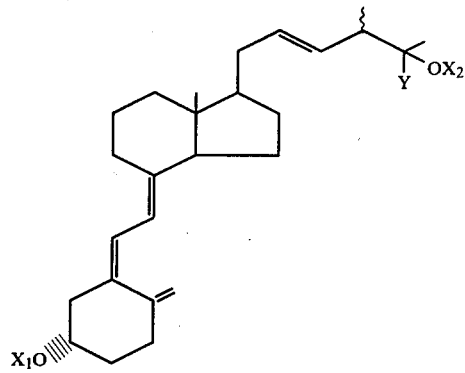

wherein $X_1$ and $X_2$ are each selected from hydrogen or acyl and Y is an alkyl or aryl group
which comprises
subjecting a 5,7-diene steroid of the formula

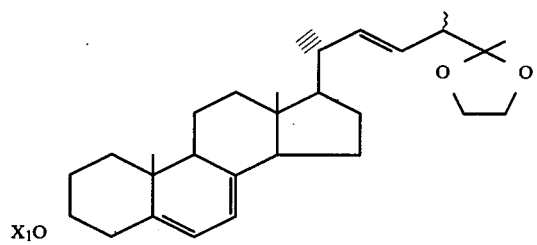

where $X_1$ is hydrogen or acyl, to acid catalyzed hydrolysis to remove the ketal group and obtain the corresponding 25-ketone, subjecting said ketone to irradiation with ultraviolet light to obtain the corresponding previtamin D compound, isomerizing said previtamin D compound in an inert solvent at a temperature from about room temperature to about 100° C. for a time sufficient to reach equilibrium, thereby obtaining a vitamin D compound of the formula

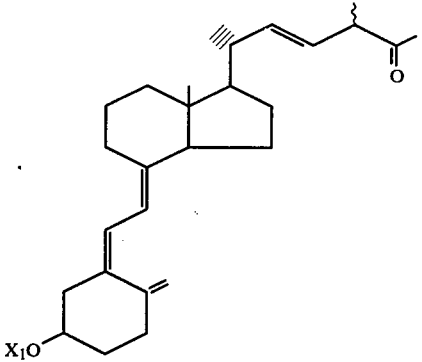

where $X_1$ is hydrogen or acyl,
reacting said vitamin D compound with a reagent of the formula YMg-halide or YLi wherein Y is an alkyl or aryl group and the halide is chloride, bromide or iodide, and, optionally, acylating one or both free hydroxy groups.

32. The process of claim 31 wherein $X_1$ and $X_2$ are hydrogen and Y is methyl.

33. A process for preparing compounds having the formula

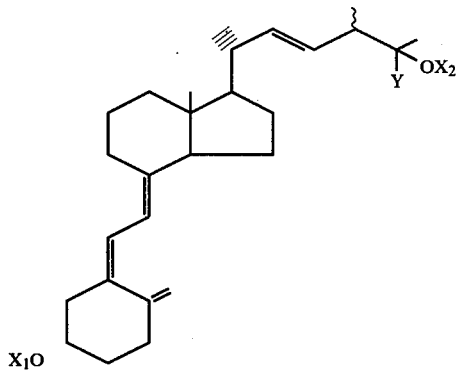

wherein $X_1$ and $X_2$ are each selected from hydrogen or acyl and Y is an alkyl or aryl group, which comprises subjecting a 5,7-diene steroid of the formula

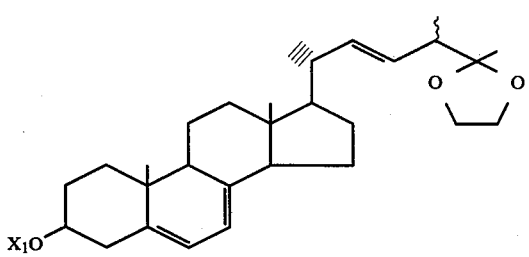

where $X_1$ is hydrogen or acyl, to acid catalyzed hydrolysis to remove the ketal group and obtain the corresponding 25-ketone, reacting the said 25-ketone with a reagent of the formula YMg-halide or YLi wherein Y is an alkyl or aryl group and the halide is chloride, bromide or iodide, to obtain the corresponding 25-hydroxy-5,7-diene, subjecting said 25-hydroxy-5,7-diene to irradiation with ultraviolet light to obtain the corresponding previtamin compound, isomerizing said previtamin D compound in an inert solvent at a temperature from about room temperature to about 100° C. for a time sufficient to reach equilibrium to obtain the desired vitamin D compound, and optionally, acylating one or both free hydroxy groups.

34. Compounds having the formula

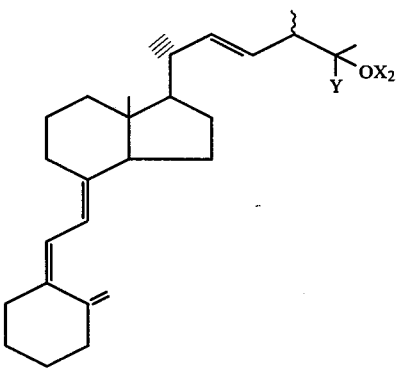

wherein $X_1$ and $X_2$ are hydrogen and Y is an isotopically labelled methyl group.

35. The compounds of claim 34 wherein Y is selected from $^{13}CH_3$, $^{14}CH_3$, $C^2H_3$ and $C^3H_3$.

* * * * *

UNITED STATES PATENT OFFICE
CERTIFICATE OF CORRECTION

Patent No. 4,448,721                    Dated May 15, 1984

Inventor(s) Hector F. DeLuca et al

It is certified that error appears in the above-identified patent and that said Letters Patent are hereby corrected as shown below:

In Column 1, before "TECHNICAL FIELD" insert -- This invention was made with Government support under NIH Grant No. AM-14881 awarded by the Department of Health and Human Services. The Government has certain rights in this invention. --

Signed and Sealed this

Twenty-third Day of October 1984

[SEAL]

*Attest:*

GERALD J. MOSSINGHOFF

*Attesting Officer*     *Commissioner of Patents and Trademarks*